United States Patent [19]
Albrecht et al.

[11] 3,983,124
[45] Sept. 28, 1976

[54] FLUORENE COMPOUNDS

[75] Inventors: William L. Albrecht; Stephen W. Horgan; Arthur D. Sill, all of Cincinnati, Ohio; Robert W. Fleming, Ann Arbor, Mich.

[73] Assignee: Richardson-Merrell Inc., Wilton, Conn.

[22] Filed: Dec. 21, 1972

[21] Appl. No.: 317,238

[52] U.S. Cl. .................. 260/293.62; 260/240 R; 260/246 B; 260/326.85; 260/556 A; 260/570.5 P; 424/248; 424/267; 424/274; 424/327; 424/330
[51] Int. Cl.² ................................. C07D 295/12
[58] Field of Search ....... 260/240 R, 246 B, 293.57, 260/293.58, 293.61, 293.62, 315, 326.85, 328, 335, 556 A, 570.5 P

[56] References Cited
UNITED STATES PATENTS

| | | | |
|---|---|---|---|
| 3,576,865 | 4/1971 | Fleming et al. | 260/559 |
| 3,592,819 | 7/1971 | Fleming et al. | 260/294.7 C |
| 3,647,860 | 3/1972 | Sill et al. | 260/475 FR |

FOREIGN PATENTS OR APPLICATIONS 764,870  3/1970  Belgium

Primary Examiner—G. Thomas Todd
Attorney, Agent, or Firm—William J. Stein; Eugene O. Retter; George W. Rauchfuss, Jr.

[57] ABSTRACT

Novel 2,7-bis-basic derivatives of fluorene, 9-fluorenol and 9-fluorenone, their preparation and use for the prevention and inhibition of virus infections are disclosed.

7 Claims, No Drawings

FLUORENE COMPOUNDS

FIELD OF THE INVENTION

This invention relates to new organic chemical compounds, to their methods of preparation, and to pharmaceutical compositions which contain these compounds as the active ingredient. The compounds described herein are useful antiviral agents which inhibit or inactivate viruses by their administration to either infected or non-infected hosts.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease, and various immunological diseases and degenerative diseases of the central nervous system have been linked with viruses as the causative agent.

At present, the control of virus infections is primarily achieved by means of immunization vaccines. For example, poliomyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines have not provided a practical solution against the wide array of infectious viruses, even where limited, as for example, to respiratory viruses alone.

One approach to the control of virus-related diseases and, particularly to the spread of such virus diseases, has been to search for medicinal agents or chemotherapeutic agents which are capable of inhibiting the growth of viruses, thereby preventing the spread of disease and preventing further damage to cells and tissues of the animal host which have not as yet been infected. Heretofore, only a limited number of virus infections such as smallpox, Asian influenza, and herpes keratitis have been prevented by chemical antiviral agents. Sulfonamides and antibiotics, which have revolutionized the treatment of bacterial infections, have substantially no effect upon virus infections. Certain infections caused by large viruses, such as lymphogranuloma venereum, psittacosis and trachoma have been successfully treated using antibiotics and sulfa drugs. However, the majority of virus infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of 2,7-bis-basic fluorenes, 2,7-bis-basic fluoren-9-ols and 2,7-bis-basic fluoren-9-ones which are particularly useful antiviral agents. These compounds are effective against a wide spectrum of virus infections and are useful in treating such infections both prophylactically and therapeutically.

Applicants' copending application, Ser. No. 23,468, filed Mar. 27, 1970, whose counterpart has been published as Belgium Patent No. 764,870 represents the closest art known to applicants and discloses ketones of fluorene useful as antiviral agents. In addition the 2,7-bis-basic ketones of fluorene, which are disclosed as preferred compounds therein, further serve as starting materials for the preparation of some of the compounds of the present invention. To applicants' knowledge the compounds described and claimed herein are novel compounds which have not been previously described nor reported in the literature. Furthermore, to applicants' knowledge no aromatic bis-oximes or bis-dioximes have heretofore been reported to have antiviral activity. The compounds of the present invention possess a wide spectrum of antiviral activity in varying degrees which could not have been predicted from a knowledge of the present state of the art.

SUMMARY OF THE INVENTION

This invention relates to new derivatives of fluorene, to their methods of preparation, compositions thereof and to their usefulness as pharmaceutical agents. More particularly, the compounds of the present invention are 2,7-bis-basic-fluorenes, 2,7-bis-basic-fluoren-9-ols and 2,7-bis-basic fluoren-9-ones, which are useful as anti-viral agents. Still more particularly, the compounds of the present invention are represented by the following structural formula:

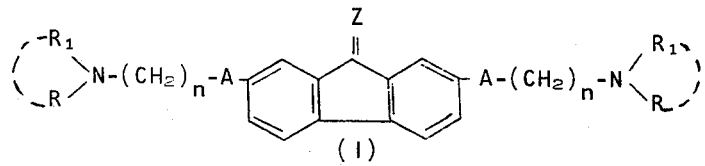

(I)

wherein A is selected from the group consisting of $CH_2$,

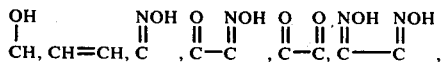

and a sigma bond; $n$ is an integer of from 1 to 4; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group, and when R and $R_1$ are taken together with the nitrogen atom to which they are attached, they represent the pyrrolidinyl, piperidino or the morpholino radical; Z is selected from the group consisting of $H_2$, O and H(OH) with the proviso that when Z is H(OH), the symbol A can only represent $CH_2$,

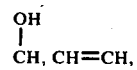

or a sigma bond; and their pharmaceutically acceptable acid addition salts.

The compounds within the scope of the present invention as represented by the above general formula include both the free base form as well as pharmaceutically acceptable acid addition salts thereof. In general, such salts are crystalline materials which are soluble in water and various hydrophilic organic solvents, and which, in comparison to their free base forms, generally demonstrate higher melting points and exhibit an increased stability.

In general, the bis-basic fluorene derivatives of the present invention are prepared by the oxidation and/or reduction of the corresponding bis-basic ketones of fluorene (II), which are fully described in copending application, Ser. No. 23,468, filed Mar. 27, 1970, and whose counterpart has been published as Belgium Patent No. 764,870. The preparation of the various classes of compounds described and claimed herein can be schematically represented as follows:

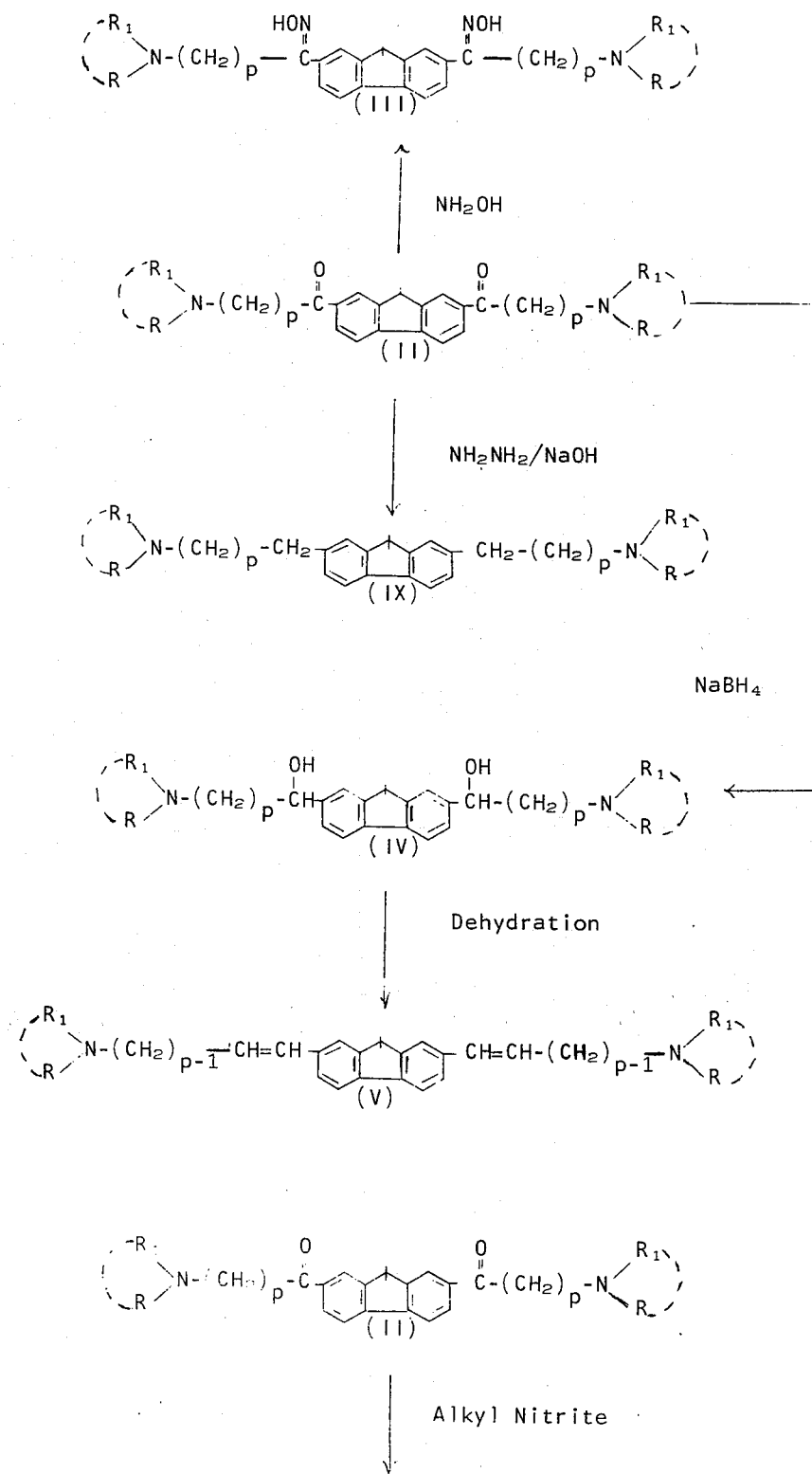

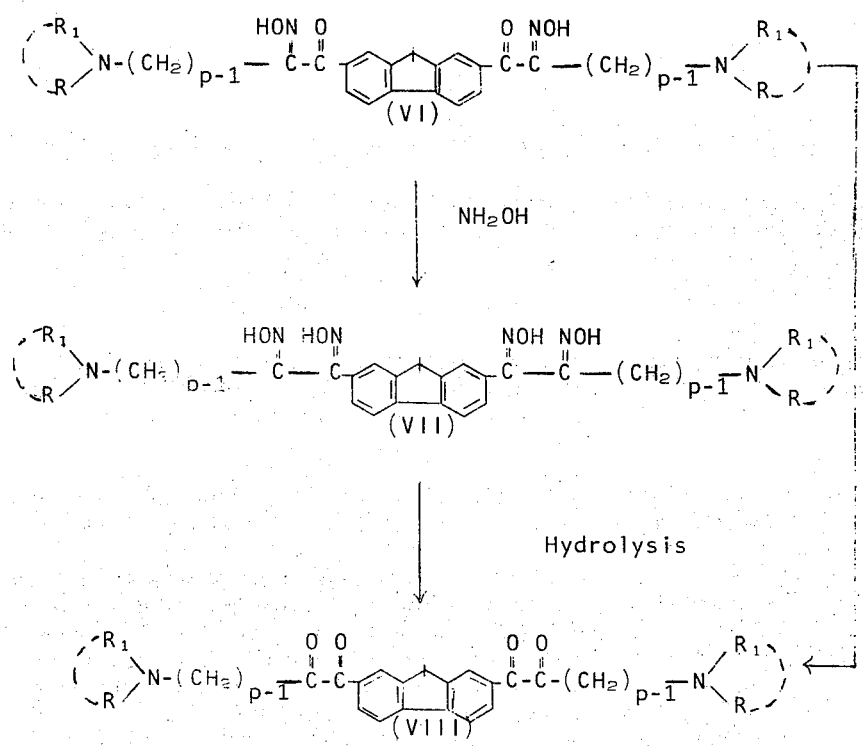

in the above reaction sequence R and $R_1$ have the values previously assigned and $p$ is an integer of from 1–5.

The 2,7-bis-basic fluoren-9-ones (I), wherein Z is oxygen, are prepared by the oxidation of the corresponding 2,7-bis-basic fluorenes or 2,7-bis-basic fluoren-9-ols, wherein Z is hydrogen and H(OH), respectively, in accordance with the procedure of Y. Sprinzak, J. Am. Chem. Soc. 80, 5449 (1958). The oxidation to the fluoren-9-ones is highly selective and is readily accomplished by bubbling oxygen through a pyridine solution containing the fluorene or fluorenol derivative in the presence of a catalytic quantity of benzyltrimethylammonium hydroxide. Thus, all of the fluorene derivatives in general formulas II–IX illustrated above as well as the fluoren-9-ol derivatives in general formulas XI and XII illustrated below are capable of being converted to their corresponding 2,7-bis-basic fluoren-9-ones via this procedure.

The fluoren-9-ol derivatives are obtained by a reduction of the corresponding fluoren-9-one derivatives. In general, either one of two methods can be employed depending upon the length of the particular side chain desired. The 2,7-bis-basic methyl fluoren-9-ols, i.e., (I) wherein Z is H(OH), A is a sigma bond and $n$ is equal to 1, are prepared by a lithium aluminum hydride reduction of the corresponding 2,7-bis-carboxamides of fluoren-9-one as illustrated in the following reaction scheme:

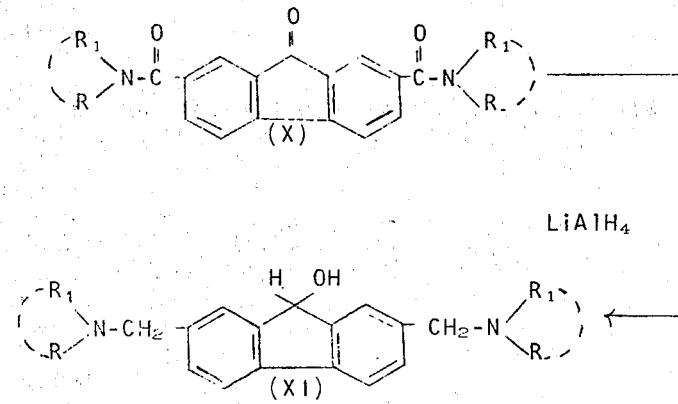

Alternatively, where a longer and more varied side chain is desired, the corresponding fluoren-9-ones are reduced using either lithium borohydride or sodium borohydride as illustrated in the following reaction scheme:

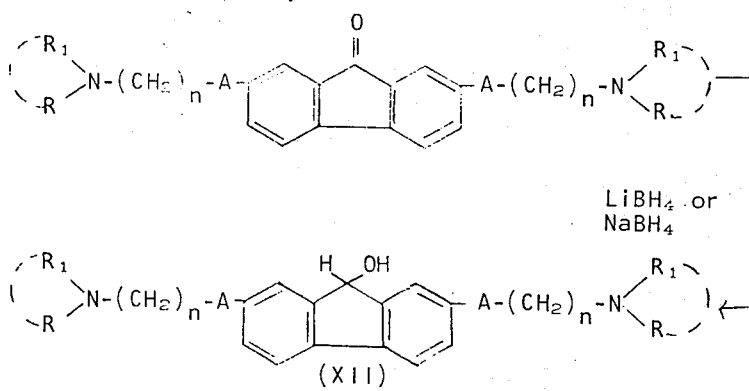

In the above reaction scheme the symbols n, R and $R_1$ have the values previously assigned, whereas the symbol A has the proviso limitation earlier mentioned. Thus, the preparation of the fluoren-9-ols (XI and XII) above is limited to those starting materials in which A is selected from the group consisting of $CH_2$, CH(OH), CH=CH or a sigma bond. In other words, those fluoren-9-ones already containing a ketone or oxime in their side chain will not survive further reduction, and other methods, not included in the present invention, must be employed for their preparation. Thus, the preparation of the fluoren-9-ol compounds of the present invention is limited only to those compounds wherein the symbol A is either $CH_2$, CH(OH), CH=CH or a sigma bond.

As can be further seen in the above reaction sequence, dehydration of the 2,7-bis-basic alkanol derivatives (IV) results in the formation of 2,7-bis-basic vinylene derivatives of fluorene (V). It is also apparent that further treatment of the 2,7-bis-basic-α-keto-β-hydroxyimino derivatives (VI) with hydroxylamine results in the formation of 2,7-bis-basic-α,β-dioxime derivatives of fluorene (VII), whereas, on the other hand, hydrolysis of the 2,7-bis-basic-α-keto-β-hydroxyimino derivatives of fluorene (VI) results in the formation of 2,7-bis-basic-α,β-diketones of fluorene (VIII).

To achieve an antiviral effect the compounds of this invention are preferably administered to a suitable host using a variety of compositions. Such compositions may be administered either prior to infection, as a prophylactic use or treatment, or they may be therapeutically administered subsequent to infection, as a curative use or treatment. The compounds of this invention may also be applied externally or topically directly at the situs of infection, or they may be administered internally or systemically irrespective of whether the treatment is prophylactic or curative in nature. In either event, replication of the infectious virus is inhibited or prevented with the concomitant result that the various disease symptoms characteristic of the pathogenic virus infection are no longer present.

DETAILED DESCRIPTION OF THE INVENTION

As can be seen from general formula (I) and its description above, the compounds of the present invention include basic side chains in the 2 and 7-positions of a fluorene, fluoren-9-ol and fluoren-9-one nucleus. These basic side chains can be regarded as consisting essentially of a bridging function connected directly to the aromatic nucleus, a basic amino group,

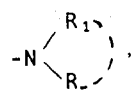

at the terminal end of said basic side chain, and an alkylene chain, $-(CH_2)_n-$ separating the bridging function from the basic amino group.

The basic amino group is a primary, secondary or tertiary amino group. Preferably each of the amino groups represented by the symbol

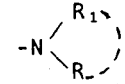

is a tertiary amino group. The symbols R and $R_1$ represent either hydrogen or a lower alkyl group. The term lower alkyl as used with regard to the basic amino groups includes groups having from 1 to 6 carbon atoms. Illustrative of such groups are both straight and branched chain alkyl groups, as for example: methyl, ethyl, n-propyl, isopropyl, n-butyl, sec-butyl, tert-butyl, isoamyl, n-pentyl and n-hexyl. When R and $R_1$ each represent lower alkyl, a preferred subgenus is formed. Each R and $R_1$ of the basic amino function also represents a cycloalkyl group having from 3 to 6 carbon atoms. Such groups include the cyclopropyl, cyclobutyl, cyclopentyl and cyclohexyl radicals.

The symbols R and $R_1$ also represent an alkenyl group having from 3 to 6 carbon atoms. In addition, the unsaturation present in this group must be in a position other than the 1-position of the alkenyl group inasmuch as any unsaturation at this point is readily hydrolyzable. Illustrative of such groups are the allyl, 3-butenyl and the 4-hexenyl radicals.

R and $R_1$ may also represent various saturated, monocyclic, heterocyclic radicals when taken in conjunction with the amino nitrogen atom to which they are attached. Typical of such heterocyclic groups are the pyrrolidinyl, piperidino and morpholino radicals. Compounds containing such groups are readily prepared and typify saturated, monocyclic, heterocyclic radicals which are generally useful in lieu of the dilower alkylamino groups present in the compounds of this invention.

The 2,7-bis-basic fluorenes, fluoren-9-ols and fluoren-9-ones described herein contain alkylene chains of various lengths ranging from 1 to a total of 4 carbon atoms as is indicated by the group $-(CH_2)_n-$ in general formula (I) above. The alkylene group may be either a straight or a branched chain and each alkylene group may be the same or different; preferably, however, both groups are the same. Illustrative of such alkylene groups are methylene, ethylene, propylene, isopropylene and butylene.

The expression "sigma bond" is intended to refer to the ordinary single bond linkage between two adjacent carbon atoms, resulting from the overlap of their corresponding orbitals. Hence, where the symbol A represents a sigma bond, the remainder of the side chain,

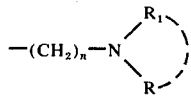

is directly attached to the 2 and the 7-positions of the fluorene nucleus. Thus, where A is the sigma bond and n is 1, the alkylene chain connecting the benzenoid nucleus with the basic amino group is methylene. On the other hand, the maximum chain length of 6 carbon atoms is obtained where n is the integer 4 and A is either

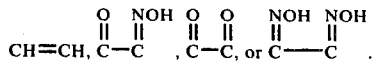

Illustrative of the 2,7-bis-basic fluorene compounds of the present invention represented by general formula (I) above, there can be mentioned: 2,7-bis(piperidinomethyl)fluorene, 2,7-bis(4-piperidinobutyl)fluorene, 2,7-bis(5-diethylaminopentyl)fluorene dihydrochloride, α,α'-bis(3-piperidinopropyl)-2,7-fluorenedimethanol, α,α'-bis(4-dimethylaminobutyl)-2,7-fluorenedimethanol, 2,7-bis(4-piperidino-1-buten-1-yl)fluorene, 2,7-bis [4-(N-methyl-N-cyclohexylamino)-1-buten-1-yl]fluorene, 2,7-bis(4-piperidinobutyryl)fluorene dioxime, 2,7-bis (5-morpholinovaleryl)fluorene dioxime, 2,7-bis[2-(hydroxyimino)-4-piperidinobutyryl]fluorene dihydrochloride 2,7-bis[2-(hydroxyimino)-4-morpholinobutyryl]fluorene dihydrochloride, 2,7-bis[2-(hydroxyimino)-5-morpholinovaleryl]fluorene dihydrochloride, 2,7-bis[2-(hydroxyimino)-4-dibutylaminobutyryl]fluorene dihydrochloride, 2,7-bis(1,2-dioxo-4-piperidinobutyl)fluorene dihydrochloride, 2,7-bis(4-dimethylamino-1,2-dioxobutyl) fluorene dihydrochloride, and 2,7-bis[2-(hydroxyimino)-4-piperidinobutyryl]fluorene dioxime.

The 2,7-bis-basic fluoren-9-ols of the present invention represented by general formula (I) above, include such specific compounds as: 2,7-bis(diethylaminomethyl)fluoren-9-ol, 2,7-bis(piperidinomethyl) fluoren-9-ol, 2,7-bis(diallylaminomethyl)fluoren-9-ol, 2,7-bis(4-dibutylaminobutyl)fluoren-9-ol, 2,7-bis (5-dimethylaminopentyl)fluoren-9-ol, α,α'-bis(3-piperidinopropyl)-9-hydroxyfluoren-2,7-dimethanol, α,α'-bis(4-dimethylaminobutyl)-9-hydroxyfluoren-2,7-dimethanol, 2,7-bis[4-(4-methylpiperidino)-1-buten-1-yl] fluoren-9-ol, 2,7-bis(5-morpholino-1-penten-1-yl)fluoren-9-ol, and 2,7-bis(4-diethylamino-1-buten-1-yl)fluoren-9-ol.

Illustrative of the 2,7-bis-basic fluoren-9-ones represented by general formula (I) above are for example: 2,7-bis(piperidinomethyl)fluoren-9-one dihydrochloride, 2,7-bis(diallylaminomethyl)fluoren-9-one dihydrochloride, 2,7-bis[5-(4-methylpiperidino)pentyl]fluoren-9-one dihydrochloride, α,α'-bis(4-diethylaminobutyl)-9-oxofluoren-2,7-dimethanol, 2,7-bis(4-piperidino-1-buten-1-yl) fluoren-9-one, 2,7-bis[4-(N-methyl-N-cyclohexylamino)-1-buten-1-yl] fluoren-9-one, 2,7-bis(1-hydroxyimino-4-piperidinobutyl) fluoren-9-one, 2,7-bis[2-(hydroxyimino)-4-morpholinobutyryl]fluoren-9-one, 2,7-bis(4-piperidino-1,2-dioxobutyl) fluoren-9-one dihydrochloride, and 2,7-bis[1,2-bis (hydroxyimino)-4-diethylaminobutyl]-fluoren-9-one.

The expression "pharmaceutically acceptable acid addition salts" is intended to apply to any organic or inorganic acid addition salts of the base compounds represented by formula (I) which are non-toxic. Illustrative inorganic acids which form suitable salts include hydrochloric, hydrobromic, sulfuric and phosphoric acids and acid metal salts such as sodium monohydrogen orthophosphate and potassium hydrogen sulfate. Illustrative organic acids which form suitable salts are the mono, di and tricarboxylic acids, as for example, acetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, or the sulfonic acids such as methanesulfonic acid and 2-hydroxyethanesulfonic acid. Either the mono or the di-acid salts may be formed and such salts can be present in either a hydrated or a substantially anhydrous form.

In general, the starting materials for the preparation of the compounds of the present invention are 2,7-bis-basic ketones having the general formula (II). These compounds are prepared via a Friedel-Crafts acylation of fluorene using an ω-haloacyl halide to form the corresponding bis(ω-haloacyl)fluorene. The subsequent amination of the bis(ω-haloacyl)fluorene to form the corresponding 2,7-bis-ketones takes place under a variety of conditions using either ammonia, a primary or secondary amine. For example, the bis(ω-haloacyl)fluorene can be heated with a large excess of amine, the excess amine serving as the reaction medium and hydrohalide acceptor. Alternatively, the bis(ω-haloacyl)fluorene may be heated with an amine in a suitable solvent such as toluene, dioxane or dimethylsulfoxide to effect condensation. Specific illustrations of the preparation of these compounds may be found more fully disclosed in copending application Ser. No. 23,468, filed Mar. 27, 1970 or its counterpart published as Belgium Patent No. 764,870.

The bis-basic oximes, (III) are prepared by the reaction of hydroxylamine with the 2,7-bis-basic ketones of formula (II). This reaction proceeds in from 2 to 48 hours at temperatures ranging from room temperature to about 100°C. Normally an excess of hydroxylamine is added in the form of its hydrochloride salt and the reaction conducted in a basic solvent such as pyridine or an alcohol containing sodium acetate or some other base which serves to release the hydroxylamine.

The 2,7-bis-basic α-keto-β-hydroxyimino derivatives of fluorene (VI) are prepared from their corresponding bis-basic ketones (II) by nitrosating the active methylene groups in the β-position. Thus, 2,7-bis-basic ketones (II) are dissolved in organic solvents such as methanol, ethanol, tetrahydrofuran and p-dioxane and the nitrosating agent generally added in small increments with stirring. Useful nitrosating agents include the lower alkyl nitrites such as methyl, ethyl, n-butyl, amyl or isoamyl nitrite. The reaction is generally conducted under anhydrous conditions in the presence of an excess of acid, such as gaseous hydrochloric acid, for a period of from 6 to 48 hours at or near room temperature.

The 2,7-bis-basic α,β-dioximes (VII) are prepared by the reaction of the corresponding 2,7-bis-basic α-keto-β-hydroxyimino derivatives (VI) with additional hydroxylamine hydrochloride. The reaction is conducted in alcoholic solvents or aqueous-alcohol mixtures in the presence of a base such as sodium hydroxide or pyridine and generally proceeds in from about 1 to about 24 hours at a temperature ranging from about from room temperature to about 100°C.

The bis-basic-α,β-diketones (VIII) are prepared via the hydrolysis of either the corresponding bis-basic α-keto-β-hydroxyimino derivatives (VI) or the bis-basic α,β-dioximes (VII). The hydrolysis reaction proceeds routinely in from 6 to 48 hours at tempertures ranging from about room temperature to about 100°C. in the presence of a strong acid. Suitable acids include hydrochloric or sulfuric acid present in concentrations of from about 5 to about 50%. The bis-basic α,β-diketone salts so formed are generally water soluble and can be recovered in their free base form by neutralization of the reaction mixture with subsequent extraction of the reaction mixture with an organic solvent.

The bis-basic alkanols of the type illustrated in general formula (IV) are prepared from the corresponding bis-basic ketones (II) under conditions generally applicable for the reduction of ketones to alcohols. Suitable reducing agents include metal hydride reducing agents such as lithium aluminum hydride with sodium borohydride having been found to be the reducing agent of choice. Two or more moles of sodium borohydride are generally used per mole of compound reduced, the additional borohydride serving to neutralize the salts of the bisbasic ketones to their free base forms. The reaction is conducted in various organic solvents such as methanol, tetrahydrofuran or ether for periods ranging from a few minutes to about 24 hours. In general the reactants are mixed together at temperatures of 0°C. or below, whereupon the temperature is gradually allowed to increase to 30°C. Upon completion of the reaction, the reaction mixture is treated with water and the 2,7-bis-basic alkanols are isolated by conventional methods and purified by crystallization from an appropriate organic solvent. Useful solvents include ether, benzene, chloroform, hexane or combinations thereof.

The 2,7-bis-basic vinylene derivatives (V) are prepared by the dehydration of the corresponding 2,7-bis-basic alkanols (IV) using a variety of dehydration methods as, for example, the pyrolytic elimination of the corresponding acetate and xanthate derivatives or, as is more generally employed, the acid catalyzed elimination of water. The later method employs treating a solution of the 2,7-bis-basic alkanol with heat. Suitable solvents include ethanol and ethylene glycol with dehydration temperatures ranging from about 70° to 120°C. Preferred acid catalysts include concentrated hydrochloric or sulfuric acid. Reaction times vary from a few minutes to several hours. The product may be obtained in the form of a salt directly from the reaction mixture, or, alternatively, as the free base by treatment of the reaction mixture with dilute alkali, followed by extraction of the free base into an organic solvent such as diethyl ether.

The 2,7-bis-basic alkanes (IX) are prepared from the corresponding 2,7-bis-basic ketones (II) via the general reaction conditions of the Wolff-Kishner reduction, utilizing hydrazine and a base catalyst in an organic solvent. The desired product can be obtained by the direct reduction of the corresponding ketone, or the reduction may proceed in a stepwise fashion by the isolation of the hydrazone intermediate which is then subsequently reduced. In general the 2,7-bis-basic ketones are dissolved in an organic solvent such as ethanol, diethylene glycol or p-xylene to which hydrazine and sodium or potassium hydroxide or alkoxide is added. The reaction mixture is heated from about 140° to about 180°C for a period of from 12 to 48 hours to form the desired 2,7-bis-basic alkanes of fluorene.

As previously mentioned, the 2,7-bis-basic fluoren-9-one derivatives are prepared by the oxidation of the corresponding fluorene bis-basic compounds in accordance with the following reaction scheme.

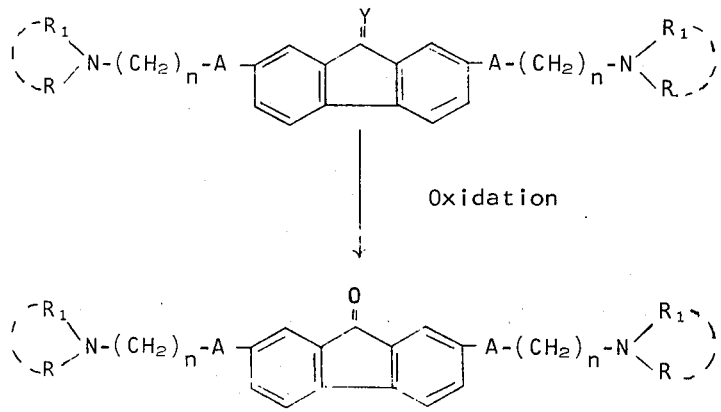

wherein the symbols A, R, $R_1$ and $n$ have the same values previously assigned and the symbol Y can only be hydrogen or H(OH). Oxygen is bubbled through a pyridine solution of the 2,7-bis-basic fluorene or 2,7-bis-basic fluoren-9-ol derivative, containing a catalytic quantity of benzyltrimethylammonium hydroxide. The reaction is conducted at room temperature for a period of from 1 to 24 hours. Other strong bases, such as alcoholic potassium hydroxide, sodium methoxide and potassium tert-butoxide, which are capable of forming a carbanion at the 9-position of the fluorene nucleus, can be used in place of the benzyltrimethylammonium hydroxide. In addition to pyridine such solvents as acetone, dimethyl sulfoxide, t-butyl alcohol and dimethylformamide may also be employed.

The 2,7-bis-basic fluoren-9-ols prepared by the chemical reduction of the corresponding base form of the 2,7-bis-basic fluorenone derivatives previously indicated in the reduction of the 2,7-bis-basic ketones of fluorene. The 2,7-bis-basic methyl fluoren-9-ol derivatives represented by general formula (1), i.e., where A is a sigma bond and n is the integer 1, are prepared by the chemical reduction of the corresponding 2,7-bis-basic carboxamides of fluoren-9-one. These carboxamides are prepared by the reaction of 9-oxofluorene-2,7-dicarbonyl chloride with various amines including ammonia, primary and secondary amines. Treatment of the carboxamides with lithium aluminum hydride results in the formation of the desired fluoren-9-ols. Further reduction of the acid addition salts of these compounds may be carried out using hydrogen and a hydrogenation catalyst, such as palladium or platinum, either supported or non-supported, resulting in the formation of the corresponding 2,7-bis-basic methyl derivatives of fluorene. A variety of solvents are suitable for hydrogenation among which water, methanol, ethanol, dimethylformamide, or mixtures thereof have been successfully employed.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Ilustratively such hosts include: birds, mice, rats, guinea pigs, gerbils, ferrets, dogs, cats, cows, horses and humans. Other viable biological materials, such as that used in the production of vaccines, may also act as a host. Thus, tissue cultures prepared from organ tissues, such as mammalian kidney or lung tissue, as well as tissue cultures prepared from embryo tissue, such as obtained from amniotic cells and chick allatoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as the influenza $A_2$ (Jap/305 virus; arboviruses, such as Semliki forest virus; the herpes group of viruses, including herpes simplex; and the poxviruses, as for example, vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ of from 5 to 50, delay or prevent completely the onset of death. Salts of these compounds of the present invention are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used in each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated with a side by side comparison of the treated surviving animals and the untreated control group of animals.

Respiratory viruses, such as influenza $A_2$ (Jap/305) virus, which are also lethal to the test animals employed, are adiministered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-inducte infection in the mouse, or perhaps due to some genetic factor or other natural defense mechanism not presently understood. For this reason the control group selected is of sufficient size so as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vacinnia infection. Tail lesions are subjectively scored on the eighth day following infection against untreated animals, which serve as a control group. The compounds of the present invention have been found to be effective in varying degrees against one or all of these test viruses.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce the formation of a virus inhibiting substance, which inhibits in some yet unknown manner the intracellular replication of the virus without appearing to have any inactivation effect per se upon the virus. A few of the viruses susceptible to interferon replication inhibition are described in Horsfall and Tamm, "Viral and Rickettsial Infections of Man", 4th Edition (1965), J.B. Lippincott Company, pp. 328–9.

As previously indicated, the compounds of the present invention may be prophylactically administered in order to prevent the spread of contagious viral diseases, or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they be administered within about 1 or 2 days following infection of the host in order to obtain the maximum therapeutic effect.

The dosage administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively, dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg of about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, i.e., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and polyethylene alcohols either with or without the addition of a surfactant. In general, the preferred liquid excipients particularly for injectable preparations, include water, saline solution, dextrose and glycol solutions, such as aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A preferred method of administration for the compounds of the present invention is orally either in a solid dosage form such as a tablet or capsule, or in a liquid form such as an oral elixir, suspension, emulsion or syrup. Ordinarily, the active ingredient comprises from about 0.5% to about 10% by weight in an oral liquid composition. In such compositions, the pharmaceutical carrier is generally aqueous in nature, as for example, aromatic water, a sugar-based syrup or a pharmaceutical mucilage. For insoluble compounds, suspending agents may be added as well as agents to control viscosity, as for example, magnesium aluminum silicate or carboxymethylcellulose. Buffers, preservatives, emulsifying agents and other excipients can also be added.

For parenteral administration such as intramuscular, intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of about 12 to about 17. The quantity of surfactant in such formulations ranges from about 5% to about 15% by weight. The surfactant can be a single surfactant having the above-identified HLB, or a mixture of two or more components having the desired HLB. Illustrative of surfactants useful in parenteral formulations are the class of polyoxyethylene sorbitan fatty acid esters, as for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 005% to about 20% by weight of the total formulation, the remaining component or components consisting of liquid pharmaceutical excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably, from about 0.001% to about 0.02% by weight of the active ingredient based upon the total weight of feed intake. The active ingredients can be admixed in animal feed concentrates suitable for use by farmers or livestock growers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquidified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples.

EXAMPLE I

2,7-Bis(4-piperidinobutyryl)fluorene

To a solution of 23.6 g (0.142 mole) of fluorene and 50.0 g (0.35 mole) of 4-chlorobutyryl chloride in 1500 ml of methylene chloride chilled to −20°C., is added 39.8 g (0.298 mole) of aluminum chloride with rapid stirring. The reaction mixture is refluxed for 4 hours, stirred at room temperature for 16 hours and is poured onto an ice/concentrated HCl mixture. The organic layer is separated, washed with saturated sodium bicarbonate solution and dried over magnesium sulfate. The methylene chloride solution is filtered, evaporated to dryness, and the solid residue recrystallized from acetone to yield the desired 2,7-bis(4-chlorobutyryl)fluorene.

m.p. 172°–5°C, $\lambda_{max}^{CHCl_3}$ 329, and $E_{1cm}^{1\%}$ 971.

A mixture of 18.8 g (0.05 mole) of 2,7-bis(4-chlorobutyryl)fluorene, 34.0 g (0.4 mole) of piperidine, and 16.6 g (0.1 mole) of potassium iodide in 200 ml of butanone is stirred and refluxed for 3 days. The reaction mixture is poured into 1000 ml of water, and the solid which precipitates is filtered and recrystallized twice from chloroform-acetone to give the desired 2,7-bis(4-piperidinobutyryl)fluorene as the free base.

m.p. 157°–9°C, $\lambda_{max}^{0.1\ IN\ HCl}$ 325, and $E_{1cm}^{1\%}$ 816.

A portion of the free base is dissolved in a mixture of chloroform and butanone. The resulting solution is acidified with ethereal HCl, and the solid which precipitates is recrystallized 3 times from a methanolbutanone mixture to give the dihydrochloride salt.

m.p. 286°–8°C, $\lambda_{max}^{H_2O}$ 325; and $E_{1cm}^{1\%\ max828}$.

EXAMPLE II

2,7-Bis(4-piperidinobutyryl)fluorene dioxime

A mixture of 10.0 g (0.021 mole) of 2,7-bis(4-piperidinobutyryl)fluorene, 25.0 g (0.36 mole) of hydroxylamine hydrochloride and 250 ml of dry pyridine is heated just below the reflux temperature for a period of about 6 hours. The pyridine is removed in vacuo and the oily residue treated with an aqueous solution of sodium hydroxide. The resulting solid is filtered, washed well with water and dissolved in a minimum of an ethyl alcohol-chloroform mixture. Upon standing at room temperature for several days, the desired product separates. Recrystallization from a chloroform solution yields 2,7-bis(4-piperidinobutyryl)fluorene dioxime having a m.p. of 190°–6°C (dec.), $\lambda_{max}^{CHCl_3}$ 323; and $E_{1cm}^{1\%}$ 715.

Utilizing essentially the above procedure but substituting for the 2,7-bis(4-piperidinobutyryl)fluorene the appropriate molar equivalent amounts of 2,7-bis (5-morpholinovaleryl)fluorene or 2,7-bis(4-diethylaminobutyryl)fluorene, the corresponding 2,7-bis-dioximes: 2,7-bis(5-morpholinovaleryl)fluorene dioxide and 2,7-bis(4-diethylaminobutyryl)fluorene dioxime are obtained.

EXAMPLE III

2,7-Bis[2-(hydroxyimino)-4-piperidinobutyryl]fluorene dihydrochloride

To a solution of 10.0 g (0.021 mole) of 2,7-bis (4-piperidinobutyryl)fluorene dissolved in 100 ml of ethanol is added gaseous hydrogen chloride. Upon precipitation of the hydrochloride salt, 150 ml of a solution of 8–15% of ethyl nitrite in ethanol is added in 50 ml portions with cooling in order to maintain the reaction mixture at room temperature. The addition of hydrogen chloride gas is continued for an additional half hour and the reaction mixture stirred overnight. The resulting solid is filtered, washed with absolute alcohol and recrystallized from an aqueous methanolacetone mixture. The desired product, 2,7-bis[2-(hydroxyimino)-4-piperidinobutyryl]fluorene dihydrochloride, is obtained as a cream colored powder having a m.p. of 250°–2.5°C. (dec.), $\lambda_{max}^{H_2O}$ 340; and $E_{1cm}^{1\%}$ 508.

Following the above procedure but substituting the appropriate molar equivalent amount of 2,7-bis(4-morpholiobutyryl)fluorene and 2,7-bis(5-morpholinovaleryl) fluorene for the starting material, 2,7-bis(4-piperidinobutyryl)fluorine, results in the formation of 2,7-bis[2-(hydroxyimino)-4-morpholinobutyryl]fluorene dihydrochloride, having a m.p. 248°–50°C. (dec.); $\lambda_{max}^{H_2O}$ 340, and $E_{1cm}^{1\%}$ 504, and 2,7-bis[2-(hydroxyimino)-5-morpholinovaleryl]fluorene dihydrochloride, m.p.

248°–50°C. (dec.), $\lambda_{max}^{H_2O}$ 340; and $E_{1cm}^{1\%}$ 520, respectively.

EXAMPLE IV

2,7-Bis[1,2-bis(hydroxyimino)-4-piperidinobutyl]fluorene

A mixture of 6.03 g (0.01 mole) of 2,7-bis[2-(hydroxyimino)-4-piperidinobutyryl]fluorene dihydrochloride prepared as in Example III, 25 g (0.36 mole) of hydroxylamine hydrochloride and 250 ml of dry pyridine is heated just below reflux temperature for about 6 hours. The pyridine is removed in vacuo and the oily residue treated with an aqueous solution of sodium hydroxide. The resulting solid is filtered, washed well with water and crystallized from an ethanol-chloroform mixture to give the desired 2,7-bis[1,2-bis(hydroxyimino)-4-piperidinobutyl]fluorene.

EXAMPLE V

2,7-Bis(1,2-dioxobutyl-4-piperidino)fluorene

A solution of 2,7-bis[2-(hydroxyimino)-4-piperidinobutyryl]fluorene dihydrochloride in 1 normal hydrochloric acid is warmed on the steam bath for 30 minutes to effect hydrolysis. The solution is cooled, and made alkaline with a sodium hydroxide solution. The resulting solid which separates is filtered, washed with water and recrystallized from a mixture of chloroform-methanol to yield the desired 2,7-bis(1,2-dioxobutyl-4-piperidino)fluorene.

In the same fashion, 2,7-bis[2-(hydroxyimino)4-dimethylaminobutyryl]fluorene dihydrochloride, and 2,7-bis[2-(hydroxyimino)-5-diethylaminovaleryl]fluorene dihydrochloride, when substituted in lieu of the starting material, 2,7-bis[2-(hydroxyimino)-4-piperidinobutyryl] fluorene dihydrochloride above, results in the formation of 2,7-bis(4-dimethylamino-1,2-dioxobutyl)fluorene and 2,7-bis(5-diethylamino-1,2-dioxopentyl)fluorene, respectively.

EXAMPLE VI

α,α'-Bis(3-piperidinopropyl)-2,7-fluorenedimethanol

A solution of 24.5 g (0.052 mole) of 2,7-bis(4-piperidinobutyryl)fluorene dissolved in 400 ml of methanol is cooled to −10°C. and 3.8 g (0.1 mole) of sodium borohydride is slowly added with stirring. The reaction mixture is gradually permitted to come to room temperature and stirring continued for an additional 16 hours. The contents of the reaction mixture are poured into approximately 1 liter of water, and the resulting solid which forms is filtered, washed with water and recrystallized from a solution of benzene. Recrystallization from a benzene-ether mixture results in the preparation of α,α'-bis(3-piperidinopropyl)-2,7-fluorenedimethanol having a m.p. of 181.5°–4.0°C, $\lambda_{max}^{EtOH}$ 273, and E $_{1cm}^{1\%}$ 592.

Following essentially the same procedure but substituting the appropriate molar equivalent amounts of 2,7-bis(5-dimethylaminovaleryl)fluorene, 2,7-bis(4-diethylaminobutyryl)fluorene and 2,7-bis(diethylaminoacetyl)fluorene for the 2,7-bis(4-piperidinobutyryl) fluorene used as a starting material above, results in the formation of α,α'-bis(4-dimethylaminobutyl)-2,7-fluroenedimethanol, α,α'-bis(3-diethylaminopropyl)-2,7-fluorenedimethanol and α,α'-bis(diethylaminomethyl) 2,7-fluorenedimethanol, respectively.

EXAMPLE VII 2,7-Bis(4-piperidino-1-buten-1-yl)fluorene

A mixture of 4.7 g (0.01 mole) of α,α'-bis(3-piperidinopropyl)-2,7-fluorenedimethanol, 25 ml of concentrated hydrochloric acid and 25 ml of ethylene glycol monoethyl ether is heated at 80°C. for 5 minutes. The solution is diluted with water, made alkaline with a 20% sodium hydroxide solution and the solution is extracted with ether. The ether extract is washed with water, dried over magnesium sulfate and evaporated in vacuo. The residue is crystallized from isopropanol resulting in the preparation of crystalline 2,7-bis(4-piperidino-1-buten-1-yl)fluorene.

EXAMPLE VIII 2,7-Bis(4-piiperidinobutyl)fluorene

A mixture of 23.6 g (0.05 mole) of 2,7-bis(4-piperidinobutyryl)fluorene, 38.6 ml (0.5 mole) of an 85% hydrazine hydrate solution, 4.5 g (0.08 mole) of potassium hydroxide, 100 ml of diethylene glycol and 100 ml of p-xylene is placed in a reaction vessel equipped with a Dean-Stark trap. The mixture is heated to reflux temperature with stirring for a period of 48 hours. The xylene layer is separated on cooling, washed with water followed by a wash with a saturated sodium chloride solution, and the organic layer dried over magnesium sulfate. The xylene solution is filtered and the solvent removed in vacuo. The remaining residue is twice recrystallized from acetone yielding the desired product, 2,7-bis(4-piperidinobutyl)fluorene, having a m.p. of 108°–10°C, $\lambda_{max}^{EtOH}$ 273, and E $_{1cm}^{1\%}$ 624.

Substituting an equivalent molar amount of 2,7-bis (5-dibutylaminovaleryl)fluorene, 2,7-bis(4-dimethylaminobutyryl)fluorene, and 2,7-bis[5-(4-methylpiperidino) valeryl]fluorene in lieu of the 2,7-bis(4-piperidinobutyryl)fluorene above, results in the formation of 2,7-bis(5-dibutylaminopentyl)fluorene, 2,7-bis(4-dimethylaminobutyl)fluorene and 2,7-bis[5-(4-methylpiperidino) pentyl]fluorene, respectively.

EXAMPLE IX

N,N,N',N'-Tetraethyl-9-oxofluorene-2,7-dicarboxamide

To a solution of 61.0 g (0.2 mole) of 9-oxofluorene-2,7-dicarbonyl chloride dissolved in 600 ml of chloroform(hydrocarbon stabilized and stored over molecular sieves) is added 58.4 g (0.8 mole) of diethylamine in small increments. The solution is refluxed with stirring for an additional 4 hours, cooled, washed 3 times with water, dried over anhydrous sodium sulfate, filtered, and the volatile materials removed on a steam bath under vacuum. The resulting oil so obtained is triturated with pentane to effect solidification. The residue when recrystallized three times from ethyl acetate yields N,N,N',N'-tetraethyl-9-oxofluorene-2,7-dicarboxamide, m.p. of 142°–3°C, $\lambda_{max}^{MeOH}$ 265, and E $_{1cm}^{1\%}$ 2011.

Substituting an equivalent molar amount of piperidine or diallylamine in lieu of the diethylamine above, results in the formation of 2,7-bis(piperidinocarbonyl)-fluoren-9-one m.p. 255.5°C; and N,N,N',N'-tetraallyl-9-oxo-fluorene-2,7-dicarboxamide, m.p. 94.5°–95.5°C, $\lambda_{max}^{MeOH}$ 266, and E $_{1cm}^{1\%}$ 1650.

EXAMPLE X 2,7-Bis(diethylaminomethyl)fluoren-9-ol

A solution of 28.0 g (0.074 mole) of N,N,N',N'-tetraethyl-9-oxofluorene-2,7-dicarboxamide in 175 ml of dry tetrahydrofuran is added to 8.5 g (0.224 mole) of lithium aluminum hydride suspended in 15 ml of dry tetrahydrofuran. The reaction is mildly exothermic in nature and stirring is continued for approximately 2½ hours. Upon completion of the reaction, the reaction mixture is decomposed by the addition of 8.5 ml of water contained in 200 ml of tetrahydrofuran, followed by the addition of 8.5 of a 15% sodium hydroxide solution and, finally, by the addition of 25 ml of water. The reaction mixture is filtered, washed with additional tetrahydrofuran, and the volatiles removed in vacuo. The residue is dissolved in approximately 2 liters pentane, filtered and the volatiles removed from the filtrate in vacuo.

The light yellow viscous oil which remains is dissolved in 400 ml of methanol, filtered, and 20 ml of 10% sodium hydroxide solution is added. To this mixture is added 4.0 g (0.1 mole) of sodium borohydride. The reaction is refluxed 2 hours under a blanket of nitrogen, cooled and excess sodium borohydride decomposed with 10% hydrochloric acid solution. The reaction mixture is made alkaline to phenolphthalein with 20% sodium hydroxide, and the mixture extracted 4 times with ether. The ether extracts are combined, washed 3 times with water, dried over anhydrous magnesium sulfate, filtered and the volatile components removed in vacuo. The remaining yellow oil is dissolved in pentane filtered and concentrated to approximately one-third of its original volume. Upon standing overnight at −20°C., a pale yellow solid is obtained which is filtered, washed with cold pentane, and which after 4 recrystallizations from pentane, yields the desired 2,7-bis(diethylaminomethyl)fluoren-9-ol, m.p. 71°–3°C, $\lambda_{max}^{0.1N\ HCl}$ 282; and E $_{1cm}^{1\%}$ 531.

Following essentially the same procedure but substituting an equivalent molar amount of 2,7-bis(piperidinocarbonyl)fluoren-9-one and N,N,N',N'-tetraallyl-9-oxo-fluorene-2,7-dicarboxamide for the N,N,N′,N′-tetraethyl-9-oxofluorene-2,7-dicarboxamide above, results in the formation of 2,7-bis(piperidinomethyl)fluoren-9-ol, having a m.p. of 152.5°–3.5°C, $\lambda_{max}^{0.1N\ HCl}$ 231, and $E_{1cm}^{1\%}$ 688, and 2,7-bis(diallylaminomethyl)fluoren-9-ol hydrochloride, respectively, having a m.p. 220.5°–1.5°C, $\lambda_{max}^{0.1N\ HCl}$ 282, and $E_{cm}^{1\%}$ 531.

EXAMPLE XI

2,7-Bis(piperidinomethyl)fluorene

A mixture of 6.15 g (0.016 mole) of 2,7-bis(piperidinomethyl)fluorene-9-ol, 12.1 ml of 10% hydrochloric acid, sufficient deionized water to bring the total volume to 150 ml, and 3.0 g of 10% palladium on charcoal catalyst is placed in a Paar hydrogenation apparatus and hydrogenated at room temperature for a period of 2 hours and 45 minutes. The resulting mixture is filtered and sufficient 20% sodium hydroxide solution is added to render the mixture basic to phenolphthalein indicator. The reaction mixture is extracted four times with chloroform, the extracts combined, washed twice with deionized water, treated with charcoal, filtered, and the major portion of the solvent removed at atmospheric pressure. The residue is recrystallized twice from methanol and once again from acetone yielding 2,7-bis(piperidinomethyl)fluorene having a m.p. 135°–6°C, $\lambda_{max}^{0.1N\ HCl}$ 270, and $E_{1cm}^{1\%}$ 807.

Following essentially the same procedure but substituting an equivalent molar amount of 2,7-bis(diethylaminomethyl)fluoren-9-ol and 2,7-bis(diallylaminomethyl)fluoren-9-ol for the 2,7-bis(piperidinomethyl)fluoren-9-ol above, results in the formation of 2,7-bis(diethylaminomethyl) fluorene and 2,7-bis(diallylaminomethyl)fluorene, respectively.

EXAMPLE XII

2,7-Bis[5-(4-methylpiperidino)pentyl]fluoren-9-one dihydrochloride

A solution of 10.0 g (0.019 mole) of 2,7-bis[5-(4-methylpiperidino)pentyl]fluorene, 2.5 ml of a 40% solution of benzyltrimethylammonium hydroxide in pyridine, and 200 ml of pyridine is stirred at room temperature and oxygen bubbled through the reaction mixture at a rate of approximately 800 ml/min. for a total of 4 hours. The reaction mixture is evaporated to dryness and the residue chromatographed using neutral alumina as the substrate and chloroform as the eluting agent. The initial fraction is collected and the solvent removed in vacuo. The residue is dissolved in butanone and acidified with ethereal hydrochloric acid. The resulting solid so obtained is filtered and recrystallized twice from a methanol-butanone solution to give 2,7-bis[5-(4-methylpiperidino)pentyl]fluoren-9-one as the dihydrochloride salt having a m.p. of 241°–3°C (dec.), $\lambda_{max}^{0.1N\ HCl}$ 266, and $E_{1cm}^{1\%}$ 853.

Using essentially the same procedure but substituting an equivalent amount of 2,7-bis(diethylaminomethyl)fluorene, 2,7-bis(piperidinomethyl)fluorene and 2,7-bis(diallylaminomethyl)fluorene for the 2,7-bis[5-(4-methylpiperidino)pentyl]fluorene above, results in the formation of 2,7-bis(diethylaminomethyl)fluoren-9-one dihydrochloride m.p. 293°–4°C (dec.), $\lambda_{max}^{0.1N\ HCl}$ 262, and $E_{1cm}^{1\%}$ 2860; 2,7-bis(piperidinomethyl)fluoren-9-one dihydrochloride, m.p. greater than 320°C, $\lambda_{max}^{0.1N\ HCl}$ 263, and $E_{1cm}^{1\%}$ 2760; and 2,7-bis(diallylaminomethyl)fluoren-9-one dihydrochloride hemihydrate, m.p. 219°–20°C, $\lambda_{max}^{0.1N\ HCl}$ 263, and $E_{1cm}^{1\%}$ 2580, respectively.

EXAMPLE XIII

The antiviral activity of 2,7-bis[2-(hydroxyimino)4-piperidinobutyryl]fluorene dihydrochloride is illustrated by taking 30 mice each weighing approximately 10 to 12 gm and dividing them into two groups, a control group containing 20 animals and a test group of 10 animals. All of the animals are challenged with a fatal dose ($4LD_{50}$) of encephalomyocarditis virus. The test group of animals is treated both prophylactically and therapeutically using a parenteral composition which contains 2,7-bis[2-(hydroxyimino)-4-piperidinobutyryl]fluorene dihydrochloride as the active ingredient dissolved in a 0.15% aqueous hydroxyethylcellulose vehicle. The composition contains the active ingredient in an amount such that each dose of 0.25 ml is equivalent to a dose level of 50 mg per kg. The control group receives a subcutaneous placebo containing the same volume of vehicle without, of course, the active ingredient. Observations over a ten day period show a termination of all of the control animals within a period of from 4 to 5 days, with the treated group of animals surviving for a statistically greater period of time.

EXAMPLE XIV

An illustrative preparation of 10,000 tablets, each containing 100 mg of 2,7-bis[2l-(hydroxyimino)-4-piperidinobutyryl]fluorene dihydrochloride is prepared as follows:

|   | Gm. |
|---|---|
| 2,7-bis[2-(hydroxyimino)-4-piperidinobutyryl]fluorene dihydrochloride | 1000 |
| Lactose | 1000 |
| Starch paste (10% w/v starch in water) | 100 |
| Starch | 32.5 |
| Calcium stearate | 6.5 |

The active ingredient is uniformly mixed with the lactose and granulated by the addition of the starch paste. The granules which form are dried at 120°F for 20 hours and forced through a No. 16 screen. The granules are lubricated by the addition of the starch and calcium searate and compressed into tablets. Each tablet so prepared contains 100 mg of the active ingredient.

EXAMPLE XV

An illustrative composition for the preparation of 1000 two-piece hard gelatin capsules, each capsule containing 100 mg of 2,7-bis(4-piperidinobutyryl)fluorene dioxime is prepared as follows:

|   | Gm. |
|---|---|
| 2,7-bis(4-piperidinobutyryl) fluorene dioxime | 100 |
| Corn starch | 150 |
| Magnesium stearate | 25 |
| 1000 hard gelatin cpasules | |

The finely powdered ingredients are mixed until uniformly dispersed and then filled into hard shelled gelatin capsules of the appropriate size.

In a similar fashion, soft gelatin capsules may be prepared in which the above composition can be granulated, slugged or directly compressed in a rotary die or plate mold in which the soft gelatin capsule is formed. Alternatively, the above excipients may be omitted and the active ingredient dispensed as a powder directly into the soft gelatin capsule.

EXAMPLE XVI

A 2% weight per volume syrup of 2,7-bis(diethylaminomethyl)fluoren-9-ol is prepared by the usual pharmaceutical techniques in accordance with the following formula:

|  | Gms. |
|---|---|
| Finely divided 2,7-bis(diethyl-aminomethyl)fluoren-9-ol | 2.0 |
| Sucrose | 33.3 |
| Chloroform | 0.25 |
| Sodium benzoate | 0.4 |
| Methyl p-hydroxybenzoate | 0.02 |
| Vanillin | 0.04 |
| Glycerol | 1.5 |
| Purified water to 100.0 ml |  |

EXAMPLE XVII

One thousand grams of an ointment for topical application containing 1.0% of 2,7-bis[5-(4-methylpiperidino)pentyl]fluoren-9-one dihydrochloride is prepared from the following ingredients:

|  | Gms. |
|---|---|
| 2,7-bis[5-(4-methylpiperidino)pentyl]fluoren-9-one dihydrochloride | 10 |
| Light liquid petrolatum | 250 |
| Wool fat | 200 |
| White petrolatum q.s. ad | 1000 |

The wool fat, white petrolatum and 200 gms of the light liquid petrolatum are liquified and held at 110°F. The active ingredient is mixed with the remaining liquid petrolatum and passed through a colloid mill. After passing through the mill, the mixture is stirred into the melt, and the melt is permitted to cool with continued stirring until congealed.

EXAMPLE XVIII

An illustrative composition for an emulsion which is parenterally injectable is as follows:

| Each ml Contains | Ingredients | Amount |
|---|---|---|
| 50 mg | 2,7-bis[2-(hydroxyimino)-5-morpholinovaleryl]fluorene dihydrochloride | 1.000 g |
| 100 mg | Polyoxyethylene sorbitan monooleate | 2.000 g |
| 0.0064 | Sodium chloride | 0.128 g |
|  | Water for injection, q.s. ad | 20.000 ml |

The parenteral composition is prepared by dissolving 0.64 g of sodium chloride in 100 ml of water suitable for injection. The polyoxyethylene sorbitan monoolate is mixed with the active ingredient, and an amount of the previously prepared aqueous sodium chloride solution added which is sufficient to bring the total volume to 20 ml. The resulting solution is shaken and autoclaved for 20 minutes at 110°C at 15 p.s.i.g. steam pressure. The composition can be dispensed in a single ampule for use in multiple dosages or it can be dispensed as 10 or 20 individual ampules for use as a single dosage unit.

We claim:
1. A 2,7-bis-basic fluorene having the formula:

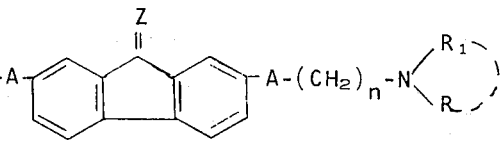

wherein A is selected from the group consisting of $CH_2$,

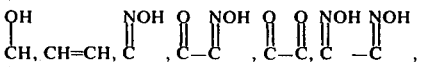

and a sigma bond; n is an integer of from 1 to 4; R and $R_1$ are each selected from the group consisting of lower alkyl having from 1 to 6 carbon atoms, cycloalkyl having from 3 to 6 carbon atoms, alkenyl having from 3 to 6 carbon atoms in which the unsaturation is in a position other than the 1-position of the alkenyl group, and when R and $R_1$ are taken together with the nitrogen atom to which they are attached they represent the pyrrolidinyl, piperidino or the morpholino radical; Z is selected from the group consisting of $H_2$, O, and H(OH) with the proviso that when Z is H(OH), the symbol A can only represent $CH_2$, $$\overset{OH}{\underset{|}{CH,}}$$

CH=CH or a sigma bond; and the pharmaceutically acceptable acid addition salts thereof.

2. A compound of claim 1 in which A is the radical

3. A compound of claim 1 in which A is the radical

4. A compound of claim 1 in which A is a sigma bond.

5. The compound 2,7-bis[2-(hydroxyimino)-4-piperidinobutyryl]fluorene and the pharmaceutically acceptable acid addition salts.

6. The compound 2,7-bis(4-piperidinobutyryl) fluorene dioxime and its pharmaceutically acceptable acid addition salts.

7. The compound 2,7-bis[5-(4-methylpiperidino)pentyl]fluoren-9-one and its pharmaceutically acceptable acid addition salts.

* * * * *